(12) United States Patent
Hubschman et al.

(10) Patent No.: US 11,660,180 B2
(45) Date of Patent: May 30, 2023

(54) INTRAOPERATIVE ASSESSMENT OF IMPLANT POSITIONING

(71) Applicants: The Regents of the University of California, Oakland, CA (US); BRIGHTECH CONSULTING, LLC, Irvine, CA (US)

(72) Inventors: Jean-Pierre Hubschman, Los Angeles, CA (US); Tsu-Chin Tsao, Los Angeles, CA (US); Matthew Gerber, Los Angeles, CA (US); Bruno Dacquay, Irvine, CA (US)

(73) Assignees: The Regents of the University of California, Oakland, CA (US); Brightech Consulting, LLC, Irvine, CA (US)

( * ) Notice: Subject to any disclaimer, the term of this patent is extended or adjusted under 35 U.S.C. 154(b) by 0 days.

(21) Appl. No.: 17/049,909

(22) PCT Filed: Apr. 24, 2019

(86) PCT No.: PCT/US2019/028937
§ 371 (c)(1),
(2) Date: Oct. 22, 2020

(87) PCT Pub. No.: WO2019/209967
PCT Pub. Date: Oct. 31, 2019

(65) Prior Publication Data
US 2021/0228333 A1    Jul. 29, 2021

Related U.S. Application Data

(60) Provisional application No. 62/662,595, filed on Apr. 25, 2018.

(51) Int. Cl.
*A61F 2/16* (2006.01)

(52) U.S. Cl.
CPC ........ *A61F 2/16* (2013.01); *A61F 2002/1681* (2013.01); *A61F 2250/0085* (2013.01);
(Continued)

(58) Field of Classification Search
CPC ................ A61F 2/16; A61F 2250/0097; A61F 2002/1681; A61F 2250/0085; A61F 2250/0096
See application file for complete search history.

(56) References Cited

U.S. PATENT DOCUMENTS

| 6,357,876 B1 * | 3/2002 | Oyama | ................. G02C 7/042 351/159.41 |
|---|---|---|---|
| 8,419,790 B1 | 4/2013 | Sabti | |

(Continued)

FOREIGN PATENT DOCUMENTS

| DE | 102016218312 A1 * | 3/2018 |
|---|---|---|
| EP | 2 111 822 A2 | 10/2009 |

OTHER PUBLICATIONS

International Preliminary Report on Patentability on PCT PCT/US2019/028937 dated Nov. 5, 2020 (6 pages).
(Continued)

*Primary Examiner* — Javier G Blanco
(74) *Attorney, Agent, or Firm* — Foley & Lardner LLP

(57) ABSTRACT

An intraocular implant device includes: (1) a lens portion; and (2) a peripheral portion surrounding the lens portion, wherein the peripheral portion includes multiple fiducials including a first fiducial, a second fiducial, and a third fiducial, the first fiducial, the second fiducial, and the third fiducial are positioned in the peripheral portion so that the third fiducial is displaced from a line segment connecting the first fiducial and the second fiducial.

5 Claims, 5 Drawing Sheets

(52) U.S. Cl.
  CPC ............... *A61F 2250/0096* (2013.01); *A61F 2250/0097* (2013.01)

(56) References Cited

U.S. PATENT DOCUMENTS

| | | | |
|---|---|---|---|
| 9,277,988 B1 | 3/2016 | Chu | |
| 2011/0118836 A1* | 5/2011 | Jain .......................... | A61F 2/16 623/6.43 |
| 2011/0264209 A1* | 10/2011 | Wiechmann .............. | A61F 2/14 623/6.6 |
| 2014/0343541 A1 | 11/2014 | Scott et al. | |

OTHER PUBLICATIONS

International Search Report and Written Opinion issued in PCT Application No. PCT/US2019/028937 dated Aug. 23, 2019, 8 pages.

\* cited by examiner

INTRAOPERATIVE ASSESSMENT OF IMPLANT POSITIONING

CROSS-REFERENCE TO RELATED APPLICATIONS

This application is a national stage entry under 35 U.S.C. § 371 of International Application No. PCT/US2019/028937, filed Apr. 24, 2019, which claims the benefit of U.S. Provisional Application No. 62/662,595, filed Apr. 25, 2018, the contents of which are incorporated herein by reference in their entirety.

STATEMENT OF GOVERNMENT SPONSORED RESEARCH

This invention was made with government support under EY024065 awarded by the National Institutes of Health. The government has certain rights in the invention.

TECHNICAL FIELD

This disclosure relates generally to an improved implant device including fiducials to facilitate imaging and positioning of the implant device during surgery.

BACKGROUND

An intraocular lens is a lens that is implanted in the eye for the treatment of an eye disorder, such as cataracts, myopia, or astigmatism. Incorrect positioning or orientation of an intraocular lens can adversely affect implant success in terms of adequately correcting refractive errors of the eye. Also, incorrect positioning or orientation of the intraocular lens can lead to post-implantation complications, such as posterior capsule opacities.

It is against this background that a need arose to develop the embodiments described herein.

SUMMARY

In some embodiments, an intraocular implant device includes: (1) a lens portion; and (2) a peripheral portion surrounding the lens portion, wherein the peripheral portion includes multiple fiducials including a first fiducial, a second fiducial, and a third fiducial, the first fiducial, the second fiducial, and the third fiducial are positioned in the peripheral portion so that the third fiducial is displaced from a line segment connecting the first fiducial and the second fiducial.

In some embodiments, an intraocular implant device includes: (1) a lens portion; and (2) a peripheral portion surrounding the lens portion, wherein the peripheral portion includes multiple fiducials including a first fiducial, a second fiducial, and a third fiducial, the first fiducial, the second fiducial, and the third fiducial are positioned in the peripheral portion along an optical plane of the intraocular implant device.

In some embodiments, a method of positioning an intraocular implant device includes: (1) determining an optical center of the intraocular implant device according to multiple fiducials in the intraocular implant device; and (2) determining a position of the optical center relative to a target position.

In some embodiments, a method of positioning an intraocular implant device includes: (1) determining an optical plane of the intraocular implant device according to multiple fiducials in the intraocular implant device; and (2) determining an orientation of the optical plane relative to a target orientation.

In some embodiments, a method of positioning an intraocular implant device includes: (1) determining an optical plane of the intraocular implant device according to multiple fiducials in the intraocular implant device; and (2) determining a position of the optical plane relative to a target position.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DETAILED DESCRIPTION

Embodiments of this disclosure are directed to (1) an improved implant device specifically designed to facilitate imaging and positioning, (2) a method for determining a position and an orientation of the implant device after insertion, and (3) a method to physically reposition the implant device following its initial insertion.

Figure 1:
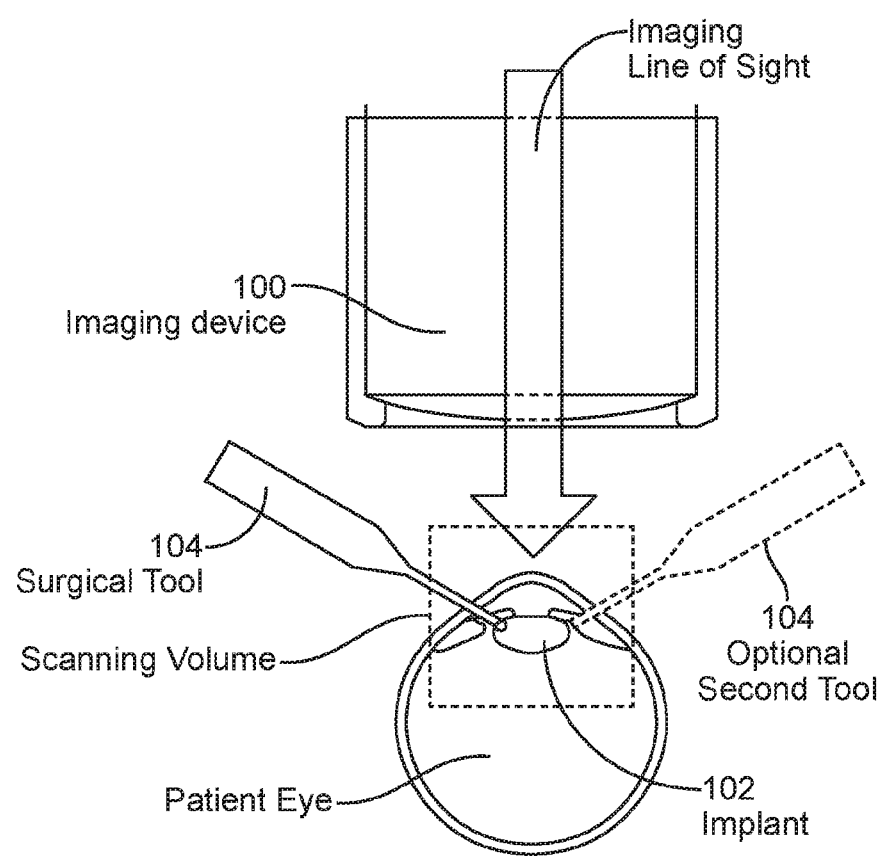
FIG. 1 illustrates an overall surgical system.

FIG. 1 illustrates an overall surgical system. An optical coherence tomography (OCT) probe, surgical microscope, or another non-contact imaging device 100 is located above the eye of a patient and is positioned to allow scanning of an entire implant device 102 as well as a surrounding ocular tissue. One or more surgical tools 104 are inserted for positioning of the implant device 102 and pass through fixed remote-center-of-motion (RCM) or "pivot" points in the eye.

Figure 2:
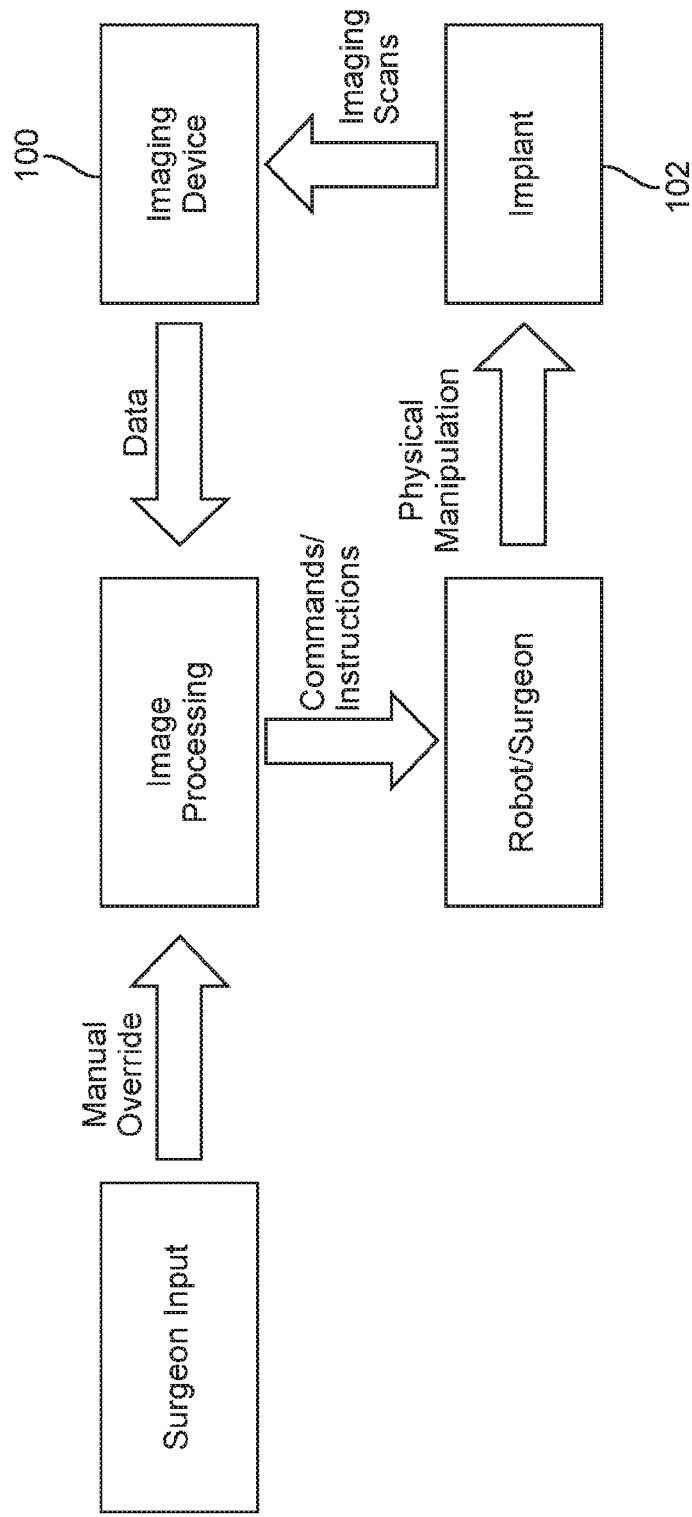
FIG. 2 illustrates an overall architecture of the surgical system of FIG. 1.

FIG. 2 illustrates an overall architecture of the surgical system. The implant device 102, located within the eye, is scanned or imaged by the OCT probe or other imaging device 100. This scan data can be processed automatically (e.g., using a processor and an associated memory with processor-executable instructions) or with manual, surgeon feedback to determine a position and an orientation of the implant device 102 with respect to the surrounding ocular tissue. This information is then interpreted and translated into commands to an automated robotic surgical device or displayed in a human-readable format to provide instructions to a surgeon. Using this information, the robotic surgical device or the surgeon can control and physically manipulate the one or more tools 104 to intraoperatively reposition the implant device 102 to a desired position and a desired orientation.

Figure 3:
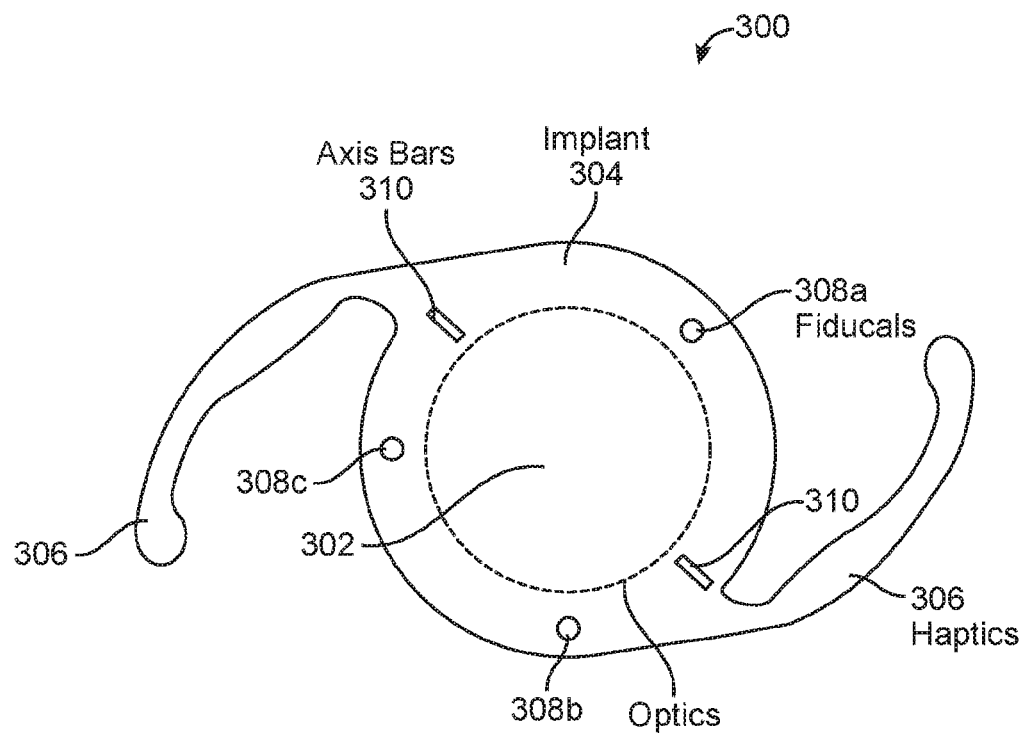
FIG. 3 illustrates an improved implant device according to some embodiments.

FIG. 3 illustrates an improved implant device 300 according to some embodiments. The implant device 300 is configured as an intraocular lens to be inserted in the eye, such as for treatment of cataracts, myopia, or astigmatism. The implant device 300 includes a lens portion 302 to focus light by refraction, and a peripheral portion 304 surrounding the lens portion 304. As shown in FIG. 3, the implant device 300 also includes a pair of side extensions 306, or haptics, extending from the peripheral portion 304 to retain the implant device 300 in place within a surrounding ocular tissue. Various portions of the implant device 300, including the lens portion 302, the peripheral portion 304, and the side extensions 306, can be integrally formed with one another as a monolithic or one-piece structure, and can be formed of, or can include, a light transmissive material, such as an acrylate polymer, a silicone, or another light transmissive polymer. Suitable light transmissive materials include those having a light transmittance over at least a portion of the visible range (e.g., at 550 nm) of at least about 70%, at least about 75%, or at least about 80%, and up to about 90% or greater, or up to about 95% or greater. The implant device 300 has an optical center, is configured to focus light along an optical axis extending through the optical center, and has an optical plane perpendicular to the optical axis.

Advantageously, the implant device 300 includes a geometric configuration of fiducials placed within or on a surface of the implant device 300. The fiducials are positioned such that they will appear in a field of view of an OCT probe or other imaging device, and can be used as points of reference to ascertain a position and an orientation of the implant device 300. The fiducials are configured so as to not interfere with a patient's vision, or optical function of the implant device 300, but are highly visible within scans or images of the imaging device.

Figure 3A:
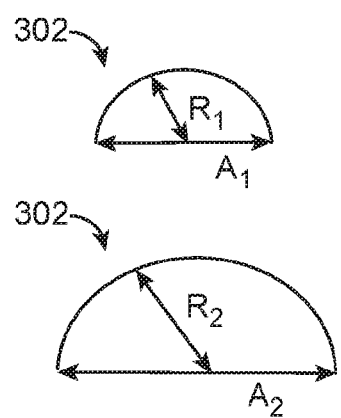
FIG. 3A illustrates a lens portion of the implant device of FIG. 3.

As shown in FIG. 3, an example of the geometric configuration of the fiducials includes three dots 308 substantially in a plane, along with two substantially collinear line segments or axis bars 310. In place of, or in combination with, the dots 308 and axis bars 310 as shown, other shapes and configurations of the fiducials as imaging or visual markings are encompassed, while providing adequate imaging or visual contrast relative to a remainder of the implant device 300. Referring to FIG. 3, the two line segments 310 are used as points of reference to rotate the implant device 300 so astigmatism correction is properly aligned. Specifically, as shown in FIG. 3A, the lens portion 302 of the implant device 300 can be shaped as a toric lens so as to be anisotropic with respect to its optical power and focal length, such as having a first axis $A_1$ (along the optical plane of the implant device 300) of greatest optical power and smallest focal length (and smallest radius of curvature $R_1$), a second axis $A_2$ (along the optical plane of the implant device 300) of smallest optical power and greatest focal length (and greatest radius of curvature $R_2$), and with the first axis $A_1$ substantially perpendicular to the second axis $A_2$. The two line segments 310 can be aligned with, for example, the first axis for astigmatism correction.

Still referring to FIG. 3, among the three dots 308, a first dot 308a and a second dot 308b are collinear along an imaginary line segment connecting the first dot 308a and the second dot 308b, and a third dot 308c is not collinear with, or is displaced from, the line segment connecting the first dot 308a and the second dot 308b. More specifically, the three dots 308a, 308b, and 308c are located as respective corners of an equilateral triangle, and a geometric center of the equilateral triangle is aligned or co-located with the optical center of the implant device 300. With the three dots 308a, 308b, and 308c serving as three points of reference on a plane (which is aligned with the optical plane of the implant device 300), a relative position, such as in terms of (x, y, z) spatial coordinates, of the optical center of the implant device 300 can be determined in relation to a surrounding anatomical tissue. In addition, ($\varphi$, $\theta$, $\psi$) angles (or another representation of orientation) can be determined based on an orientation of these three points of reference. With the position and orientation of the implant device 300 determined, and a desired position and a desired orientation used as a reference, an error between the two can be used to drive commands or instructions to a robotic surgical device or a human surgeon to intraoperatively reposition the implant device 300 to reduce the error.

Four surgically relevant cases are explained below: (1) optical centering of the implant device 300, (2) a tilt of the implant device 300 with respect to a plane of an iris, (3) adjusting an anterior/posterior position of the implant device 300 along an axis perpendicular to the plane of the iris, and (4) rotation of the implant device 300 to align for astigmatism.

Figure 4:
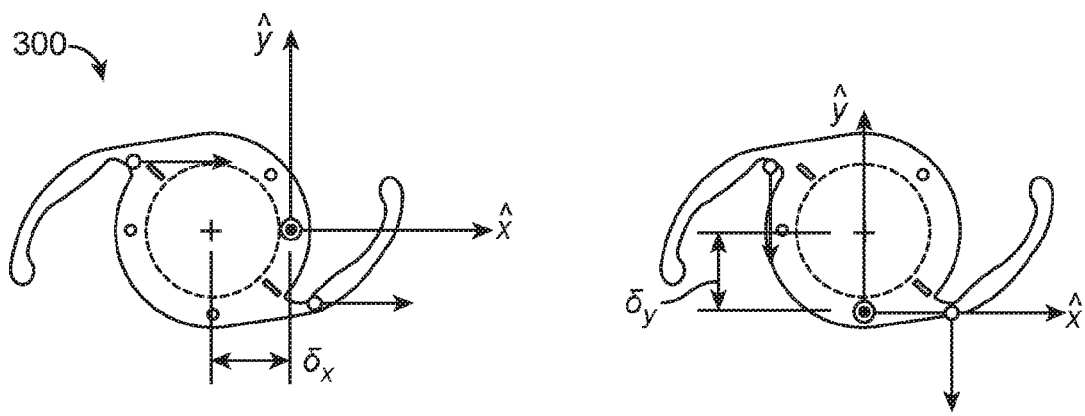
FIG. 4 illustrates repositioning of the implant device to optically center the implant device.

FIG. 4 illustrates repositioning of the implant device 300 to optically center the implant device 300. Here, an origin of a coordinate frame represents a desired or target position of the optical center of the implant device 300, and the (x, y) plane is aligned with or parallel to a plane of an iris. In the case of two surgical tools, cooperative forces can be applied as illustrated by the arrows to adjust a position of the implant device 300. In this way, $\delta_x$ and $\delta_y$ (positional error in x and y) can be cancelled by translating the implant device 300 an appropriate amount.

Figure 5:
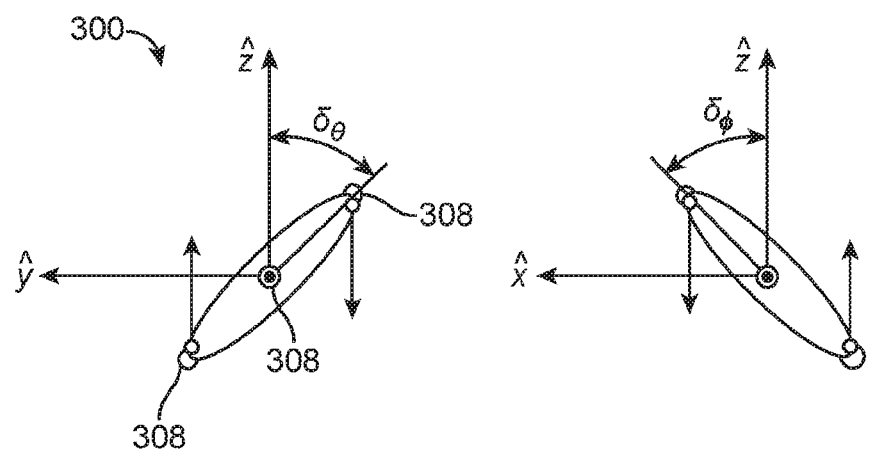
FIG. 5 illustrates reorientation of tilt angles of the implant device with respect to the iris plane.

FIG. 5 illustrates reorientation of tilt angles of the implant device 300 with respect to the iris plane. A desired or target orientation of the implant device 300 is specified with respect to the plane of the three dots 308 relative to the axes of the coordinate frame, with the z axis perpendicular to the plane of the iris. Again, translational forces can be applied as illustrated by the arrows to result in desired moments to adjust $\delta_\varphi$ and $\delta_\theta$ to desired values (orientation in $\varphi$ and $\theta$ relative to the z axis).

Figure 6:
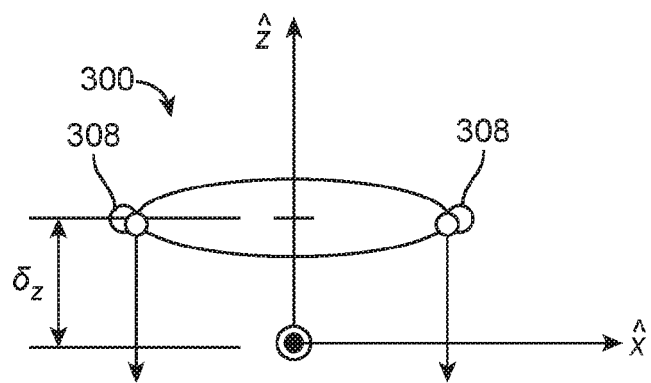
FIG. 6 illustrates repositioning of the implant device to adjust an anterior/posterior position of the implant device.

FIG. 6 illustrates repositioning of the implant device 300 to adjust an anterior/posterior position of the implant device 300. A desired or target anterior/posterior position of the implant device 300 is specified with respect to the plane of the three dots 308 relative to the origin of the coordinate frame, in terms of a distance between the plane and the origin. In the case of two surgical tools, cooperative forces can be applied as illustrated by the arrows to adjust a position of the implant device 300. In this way, $\delta_z$ (positional error in z) can be cancelled by translating the implant device 300 an appropriate amount.

Figure 7:
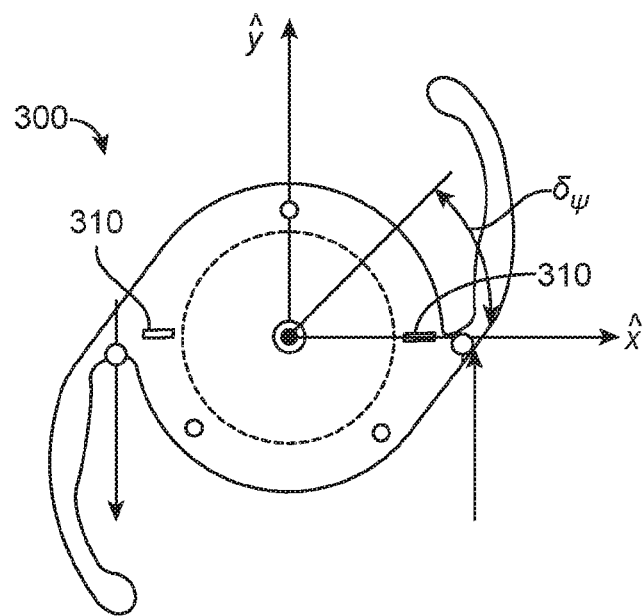
FIG. 7 illustrates rotation of the implant device to adjust an orientation of the implant device to align for astigmatism.

FIG. 7 illustrates rotation of the implant device 300 to adjust an orientation of the implant device 300 to align for astigmatism. A desired or target orientation of the implant device 300 is specified with respect to the two line segments 310 relative to the axes of the coordinate frame. In the case of two surgical tools, cooperative forces can be applied as illustrated by the arrows to adjust the orientation of the implant device 300. In this way, $\delta_\psi$ (orientation in $\psi$) can be adjusted to a desired value by rotating the implant device 300 an appropriate amount.

Embodiments of this disclosure can be used to optimally position an intraocular implant device during surgery and provide a robotic surgical device or a human surgeon with relevant information on its position and orientation to assess implant success. There are several benefits including the following. (1) With the position and orientation of the implant device determined to within a scanning resolution of an imaging device, incorrect positioning of the implant device can be reduced or eliminated, and thus allows for improved correction of refractive errors of the eye. (2) Potential post-implantation complications can be reduced, again through correct positioning of the implant device, such as posterior capsule opacities. (3) Embodiments can be used to assess that both haptics are contained within a capsular bag following insertion, and can provide information on an appropriate repositioning for correction.

Example Embodiments

The following are example embodiments of this disclosure.

First Aspect

In some embodiments, an intraocular implant device includes: (1) a lens portion; and (2) a peripheral portion surrounding the lens portion, wherein the peripheral portion includes multiple fiducials including a first fiducial, a second fiducial, and a third fiducial, the first fiducial, the second fiducial, and the third fiducial are positioned in the peripheral portion so that the third fiducial is displaced from a line segment connecting the first fiducial and the second fiducial.

In some embodiments, the first fiducial, the second fiducial, and the third fiducial are positioned in the peripheral portion so as to define a triangle, with the first fiducial, the second fiducial, and the third fiducial positioned at respective vertices of the triangle. In some embodiments, a geometric center of the triangle is aligned with an optical center of the intraocular implant device.

In some embodiments, the first fiducial, the second fiducial, and the third fiducial are positioned in the peripheral portion so as to define a plane extending through the first fiducial, the second fiducial, and the third fiducial. In some embodiments, the plane defined by the first fiducial, the second fiducial, and the third fiducial is aligned with an optical plane of the intraocular implant device and extending within the intraocular implant device.

In some embodiments, the multiple fiducials further include a fourth fiducial and a fifth fiducial, which are positioned in the peripheral portion so as to be aligned with an axis of the lens portion to correct for astigmatism. In some embodiments, the lens portion is shaped so as to be anisotropic with respect to an optical power of the lens portion, and the fourth fiducial and the fifth fiducial are positioned in the peripheral portion so as to be aligned with an axis of greatest optical power of the lens portion.

Second Aspect

In some embodiments, an intraocular implant device includes: (1) a lens portion; and (2) a peripheral portion surrounding the lens portion, wherein the peripheral portion includes multiple fiducials including a first fiducial, a second fiducial, and a third fiducial, the first fiducial, the second fiducial, and the third fiducial are positioned in the peripheral portion along an optical plane of the intraocular implant device.

In some embodiments, the optical plane of the intraocular implant device extends within the intraocular implant device.

In some embodiments, the first fiducial, the second fiducial, and the third fiducial are positioned at respective vertices of a triangle along the optical plane of the intraocular implant device. In some embodiments, a geometric center of the triangle is aligned with an optical center of the intraocular implant device.

In some embodiments, the lens portion and the peripheral portion are integrally formed.

In some embodiments, the intraocular implant device further includes multiple side extensions extending from the peripheral portion.

In some embodiments, the multiple fiducials further include a fourth fiducial and a fifth fiducial, which are positioned in the peripheral portion so as to be aligned with an axis of the lens portion to correct for astigmatism.

Third Aspect

In some embodiments, a method of positioning an intraocular implant device includes: (1) determining an optical center of the intraocular implant device according to multiple fiducials in the intraocular implant device; and (2) determining a position of the optical center relative to a target position.

In some embodiments, the method further includes directing repositioning of the intraocular implant device to translate the optical center towards the target position.

Fourth Aspect

In some embodiments, a method of positioning an intraocular implant device includes: (1) determining an optical plane of the intraocular implant device according to multiple fiducials in the intraocular implant device; and (2) determining an orientation of the optical plane relative to a target orientation.

In some embodiments, the method further includes directing repositioning of the intraocular implant device to rotate the optical plane towards the target orientation.

Fifth Aspect

In some embodiments, a method of positioning an intraocular implant device includes: (1) determining an optical plane of the intraocular implant device according to multiple fiducials in the intraocular implant device; and (2) determining a position of the optical plane relative to a target position.

In some embodiments, the method further includes directing repositioning of the intraocular implant device to translate the optical plane towards the target position.

As used herein, the singular terms "a," "an," and "the" may include plural referents unless the context clearly dictates otherwise. Thus, for example, reference to an object may include multiple objects unless the context clearly dictates otherwise.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common characteristics.

As used herein, the terms "connect," "connected," and "connection" refer to an operational coupling or linking. Connected objects can be directly coupled to one another or can be indirectly coupled to one another, such as via one or more other objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, a first numerical value can be "substantially" or "about" the same as a second numerical value if the first numerical value is within a range of variation of less than or equal to ±10% of the second numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" parallel can refer to a range of angular variation relative to 0° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, "substantially" perpendicular can refer to a range of angular variation relative to 90° that is less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, concentrations, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a range of about 1 to about 200 should be understood to include the explicitly recited limits of about 1 and about 200, but also to include individual values such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations are not a limitation of the disclosure.

What is claimed is:

1. An intraocular implant device comprising:
    a lens portion that is configured for an optical function to focus light by refraction; and
    a peripheral portion surrounding the lens portion,
    wherein the peripheral portion includes multiple fiducials including a first fiducial, a second fiducial, and a third fiducial, and wherein the peripheral portion including the multiple fiducials is configured so as not to interfere with the optical function of the lens portion,
    wherein the first fiducial, the second fiducial, and the third fiducial are positioned in the peripheral portion so that the third fiducial is displaced from a line segment connecting the first fiducial and the second fiducial,
    wherein the fiducials are configured so as to not interfere with a patient's vision through the lens portion, but are further configured to be otherwise visible in images of the implant device,
    wherein the first fiducial, the second fiducial, and the third fiducial are positioned in the peripheral portion so as to define a triangle, with the first fiducial, the second fiducial, and the third fiducial positioned at respective vertices of the triangle, and
    wherein a geometric center of the triangle is aligned with an optical center of the intraocular implant device.

2. The intraocular implant device of claim 1, wherein the first fiducial, the second fiducial, and the third fiducial are positioned in the peripheral portion so as to define a plane extending through the first fiducial, the second fiducial, and the third fiducial.

3. The intraocular implant device of claim 2, wherein the plane defined by the first fiducial, the second fiducial, and the third fiducial is aligned with an optical plane of the intraocular implant device.

4. The intraocular implant device of claim 1, wherein the multiple fiducials further include a fourth fiducial and a fifth fiducial, which are positioned in the peripheral portion so as to be aligned with an axis of the lens portion.

5. The intraocular implant device of claim 4, wherein the lens portion is shaped so as to be anisotropic with respect to an optical power of the lens portion, and the fourth fiducial and the fifth fiducial are positioned in the peripheral portion so as to be aligned with an axis of greatest optical power of the lens portion.

* * * * *